United States Patent [19]

Gupta

[11] Patent Number: 5,625,109
[45] Date of Patent: Apr. 29, 1997

[54] LIQUID PHASE DEHYDRATION OF TERTIARY BUTYL ALCOHOL

[76] Inventor: Vijai P. Gupta, 816 Newtown Rd., Berwyn, Pa. 19312

[21] Appl. No.: 342,560

[22] Filed: Nov. 21, 1994

[51] Int. Cl.⁶ .................................. C07C 1/20; C07C 1/24
[52] U.S. Cl. ...................... 585/639; 585/638; 585/640
[58] Field of Search ............................. 585/638, 639, 585/640

[56] References Cited

U.S. PATENT DOCUMENTS

| | | | |
|---|---|---|---|
| 3,510,538 | 5/1970 | Rosenthal | 585/639 |
| 4,155,945 | 5/1979 | Levine | 585/639 |
| 4,165,343 | 8/1979 | Levine et al. | 585/638 |
| 4,423,271 | 12/1983 | Obenaus et al. | 585/639 |

*Primary Examiner*—Helane Myers
*Assistant Examiner*—Walter D. Griffin
*Attorney, Agent, or Firm*—William C. Long

[57] ABSTRACT

A tertiary butyl alcohol feed is continuously dehydrated in the liquid phase, in a boiling reactor, a vapor mixture of isobutylene, water, tertiary butyl alcohol and isobutanol and/or secondary butanol is removed and cooled, isobutylene is recovered and the remaining product mixture is phase separated into an upper organic-rich phase which is recycled to dehydration and a lower aqueous phase which is purged.

3 Claims, 2 Drawing Sheets

LIQUID PHASE DEHYDRATION OF TERTIARY BUTYL ALCOHOL

FIELD OF THE INVENTION

The present invention relates to the liquid phase dehydration of tertiary butyl alcohol to form isobutylene wherein the dehydration is carried out in a boiling reactor, a vapor stream including of dehydration products is removed and cooled, isobutylene is separated, and the remaining product mixture is phase separated into an organic phase which is recycled and an aqueous phase which is purged.

DESCRIPTION OF THE PRIOR ART

The dehydration of tertiary butyl alcohol to produce isobutylene is a known reaction. In general, the reaction is carried out in the vapor phase at very high temperatures of the order of 370° C. or so which requires the use of expensive heaters and other costly hardware and which results in high energy consumption.

Liquid phase dehydration systems are also known. U.S. Pat. Nos. 3,510,538, 4,165,343 and 4,155,945 describe such systems. Generally, a benzene or xylene azeotroping agent is used to remove water from the liquid reaction system.

However, the aromatic azeotroping agents are expensive and tend to react to some extent with isobutylene, and the relatively heavy products have to be purged from the system resulting in product yield loss and possible catalyst loss, especially when a soluble catalyst such as para toluene sulfonic acid is employed.

SUMMARY OF THE INVENTION

In accordance with the present invention, tertiary butyl alcohol is continuously dehydrated in the liquid phase in a boiling reactor, the liquid reaction mixture in the boiling reactor having a substantial isobutanol and/or secondary butanol content. A vapor mixture comprised of product isobutylene, tertiary butyl alcohol, water and isobutanol and/or secondary butanol is continuously withdrawn from the reactor and cooled, isobutylene is recovered therefrom and the remainder of the mixture is phase separated with the organics being returned to the reactor. A key feature is regulation of the composition from the dehydrator such that the phase separation necessary to the invention can be accomplished.

DETAILED DESCRIPTION

The liquid phase dehydration of the tertiary butyl alcohol is carried out at conditions which are generally known for this reaction Broadly, temperatures in the range of about 70°–200° C. preferably 120°–160° C. are employed. It is generally desirable to operate at superatmospheric pressure sufficient to maintain the reaction mixture in the liquid phase while permitting vaporization of product water and isobutylene along with tertiary butyl alcohol, isobutanol and secondary butanol and removal of the same from the reaction zone. Generally, pressures range from 30–400 psig.

An acidic catalyst is employed in accordance with known procedures. Sulfonic acid cation exchange resin catalysts can be employed as can sulfuric acid. However, it is especially preferred to use organic sulfonic acid catalysts and para toluene sulfonic acid (PTSA) or methane sulfonic acid are especially useful.

The amount of catalyst is not critical; it is preferred in the case of soluble catalysts to operate with catalyst amounts below the solubility limit, e.g. 0.1–4.0 wt %, based on the entire reaction mixture.

A problem with prior liquid phase tertiary butyl alcohol dehydration procedures has been the difficulty in removing the relatively high boiling water of dehydration, which, if not removed, effectively interferes with the desired dehydration. The use of costly and reactive solvents such as xylene has not been entirely satisfactory.

Now in accordance with the present invention, the dehydration is carried out with continuous removal of a reaction vapor mixture containing the water and isobutylene products of reaction, this vapor mixture having a composition which after condensation and separation of isobutylene will undergo phase separation into an organic-rich phase and an aqueous phase which contains the water of dehydration. The organics-rich phase can be recycled to the dehydration while the aqueous phase can be purged after recovery of any organics, if desired.

Practice of the invention is especially useful for the dehydration of tertiary butyl alcohol which is formed in the Oxirane propylene oxide/tertiary butyl alcohol process. Small amounts of isobutanol, isopropanol, secbutanol, and the like are formed as impurities in the Oxirane process, thus providing a source for the materials used in the invention.

Figure 1:
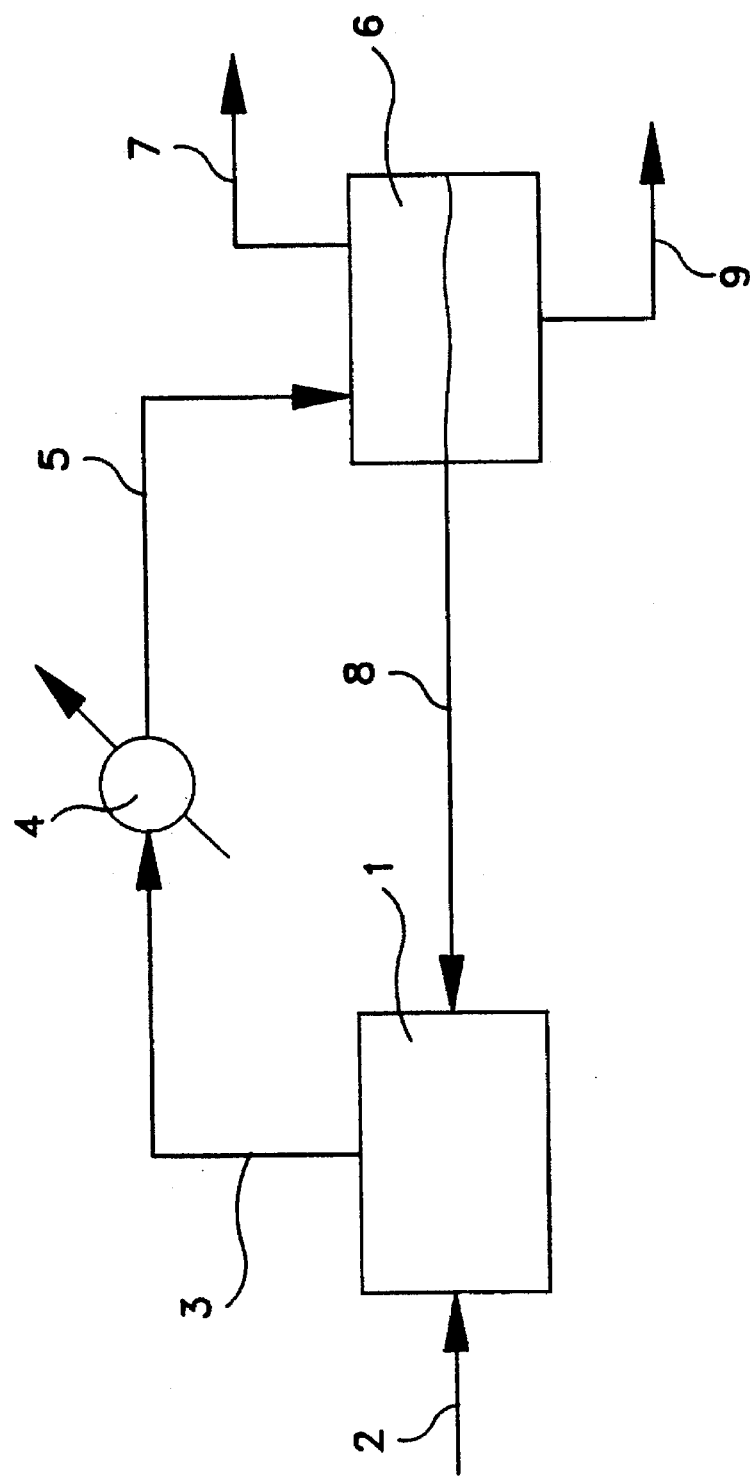
FIG. 1 illustrates schematically practice of the invention.

Practice of the invention can be described with reference to accompanying FIG. 1. Referring to FIG. 1, the tertiary butyl alcohol feed stream is continuously passed to dehydrator 1 via line 2 wherein the feedstream is subjected to reaction conditions effective for the liquid phase dehydration of tertiary butyl alcohol to isobutylene and water. Dehydrator 1 can be a CSTR or any equivalent apparatus for carrying out this reaction.

A vapor mixture comprised of product isobutylene and water together with unreacted tertiary butyl alcohol and also containing isobutanol and/or secondary butanol is separated via line 3 and passed to heat exchanger 4 wherein the vapor mixture is cooled to a temperature effective to condense the non-isobutylene components.

The cooled mixture is passed via line 5 to separation zone 6 which for purpose of illustration is shown as only a single zone where in actuality it can be plurality of zones.

From zone 6, product isobutylene vapor is separated via line 7. This product stream can, if desired, be treated for the separation of small amounts of water and organics contained therein (not shown).

The liquid components of the dehydration reaction mixture are phase separated in zone 6 into an upper organic-rich phase which is concentrated in unreacted tertiary butyl alcohol as well as in isobutanol and/or secondary butanol and a lower water-rich phase which contains the net water produced in the tertiary butyl alcohol dehydration reaction.

The tertiary butyl alcohol containing organics-rich phase passes via line 8 back to dehydration zone 1 while the water-rich phase is separated via line 9 and the net dehydration water purged after recovery of contained organics (not shown).

In order to successfully carry out the invention it is essential that the lower water-rich layer removed via line 9 contain the water formed by the dehydration reaction since recycle of such water via line 8 would cause a water build-up in dehydrator 1 which ultimately would prevent further tertiary butyl alcohol dehydration.

Figure 2:
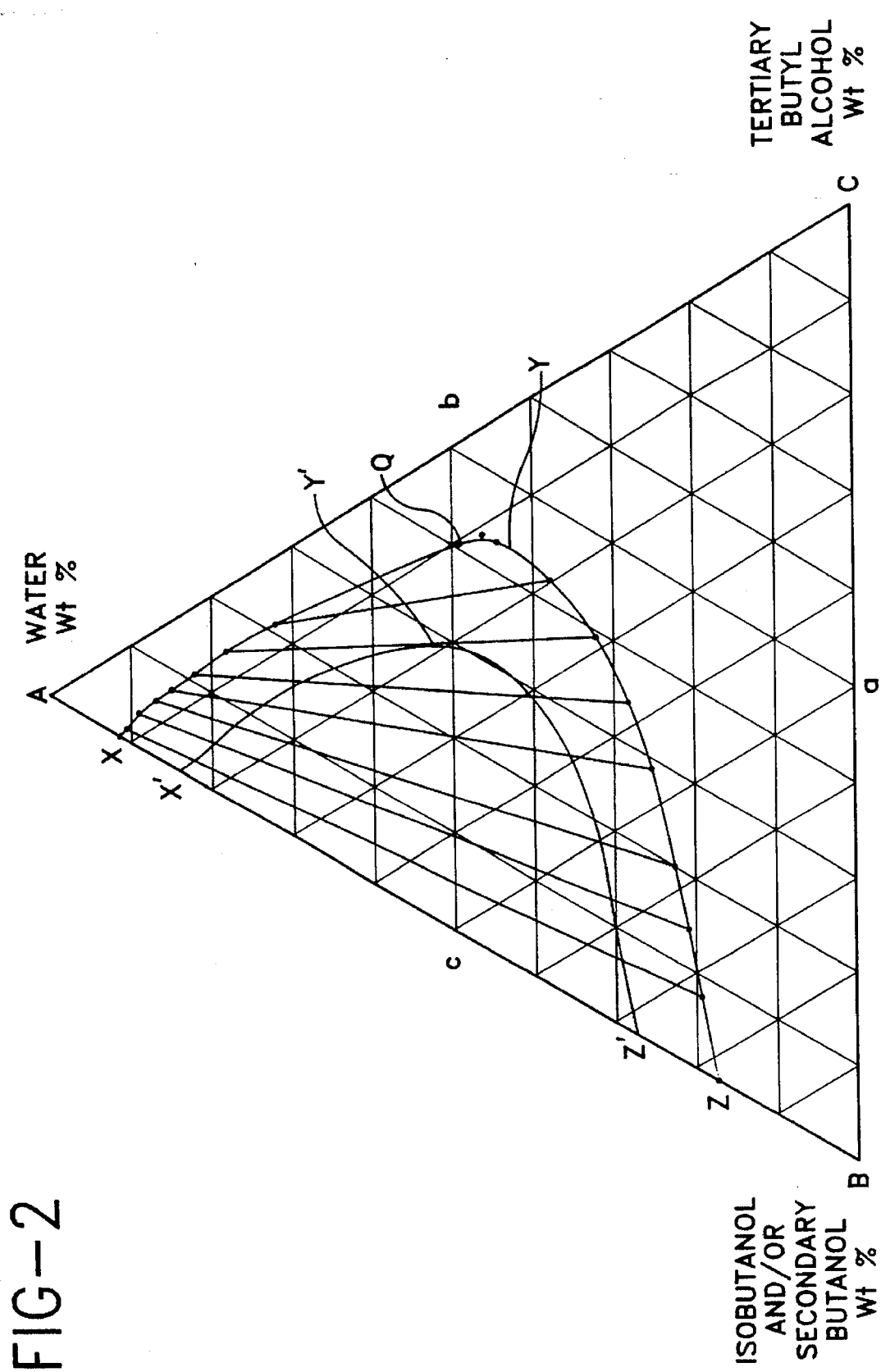
FIG. 2 is a phase diagram showing compositions which are necessary for successful practice of the invention.

For effective phase separation of the dehydration reaction mixture components after isobutylene separation, it is essential that the composition of these components be within the two phase region defined in the phase diagram of FIG. 2 by XYZ. Preferably the composition is well removed from the Plait point Q and an especially preferred composition is that designated by X'Y'Z' in FIG. 2. Because isobutanol and secondary butanol behave similarly in the system, they are treated in the phase diagram as a single component.

Composition of the reaction mixture components after isobutylene separation is regulated by the composition of the feed and recycle streams to zone 1 as well as by the conversion of tertiary butyl alcohol in zone 1 and is readily determined and regulated during practice of the invention.

Generally, it is advantageous to maintain a liquid dehydration reaction mixture composition by weight of about 5 to 30% tertiary butyl alcohol, 20 to 70% isobutanol and/or secondary butanol, 5 to 5% water and less than 5% isobutylene.

The following example illustrates the invention. Referring to FIG. 1, a tertiary butyl alcohol feedstream passes to dehydrator 1 via line 2 at the rate of 4,500 lbs/hr. This stream comprises by weight 94.5% tertiary butyl alcohol, 1.1% water, and 4.4% isobutanol. In dehydrator 1, tertiary butyl alcohol is dehydrated in the liquid phase to isobutylene and water at 160° C. and 200 psia; para toluene sulfonic acid catalyst is used, the catalyst is present in a concentration of about 2.5 wt % based on the liquid reaction mixture.

A reaction vapor mixture is continuously removed via line 3 in amount of 9,810 lbs/hr, this mixture comprised by weight of 11.5% tertiary butyl alcohol, 32.4% isobutylene, 22% water and 34% isobutanol.

Steady state composition of the liquid reaction mixture in dehydrator 1 by weight is 15% tertiary butyl alcohol, 22.5% water, 62.5% isobutanol and a trace of isobutylene.

The reaction vapor mixture is cooled in heat exchanger 4 to about 32° C. and pressure is lowered to 20 psia. The cooled mixture passes via line 5 to separation zone 6 and a product isobutylene vapor stream is separated from liquid condensation products and is removed via line 7 at the rate of 3,263 lbs/hr. This stream comprises by weight 96.4% isobutylene, 1.1% water, 1.1% tertiary butyl alcohol and 1.4% isobutanol.

The liquid reaction mixture components, after separation of the isobutylene vapor stream, comprise by weight about 0.6% isobutylene, 16.7% tertiary butyl alcohol, 32.4% water and 50.3% isobutanol. Referring to FIG. 2, it can be seen that this composition is well within area XYZ of the phase diagram. This mixture is separated in separator 6 into an upper organic-rich layer and a lower water-rich layer.

The organic-rich layer is removed via line 8 and passed to dehydrator 1 at the rate of 5,394 lbs/hr, the composition by weight of this stream being 19.3% tertiary butyl alcohol, 0.7% isobutylene, 20.5% water and 59.5% isobutanol.

The water-rich layer is removed via line 9 at the rate of 1,153 lbs/hr, the composition by weight of this stream being 4.6% tertiary butyl alcohol, 0.05% isobutylene, 88.2% water and 7.1% isobutanol.

Comparative Example

By way of contrast, in a similar operation except that the condensed reaction mixture components after isobutylene separation had the composition by weight of 59.9% tertiary butyl alcohol, 0.4% isobutylene, 27.9% water and 11.7% isobutanol, a phase separation could not be obtained as the composition was well outside area XYZ of FIG. 2.

When the condensed reaction mixture components are recycled to dehydrator 1, water rapidly builds up in the dehydrator with separation into two liquid phases. Upon purging water from the dehydrator to prevent this build-up, catalyst is also purged causing the dehydration reaction to cease.

I claim:

1. A process for the liquid phase dehydration of tertiary butyl alcohol to isobutylene which comprises subjecting tertiary butyl alcohol to catalytic liquid phase dehydration conditions in a dehydration zone, removing a vapor mixture from said dehydration zone consisting essentially of isobutylene, water, tertiary butyl alcohol and isobutanol and/or secondary butanol, cooling the separated vapor mixture to condense a mixture of tertiary butyl alcohol, water and isobutanol and/or secondary butanol, recovering isobutylene, phase separating the condensed mixture of tertiary butyl alcohol, water and isobutanol and/or secondary butanol into an organic-rich upper liquid phase and a water-rich lower liquid phase, and recycling the organic-rich Upper liquid phase to the dehydration step.

2. The process of claim 1 wherein the condensed tertiary butyl alcohol, water and isobutanol and/or secondary butanol has a composition in the area XYZ of FIG. 2.

3. The process of claim 1 wherein the condensed tertiary butyl alcohol, water and isobutanol and/or secondary butanol has a composition in the area X'Y'Z' of FIG. 2.

* * * * *

UNITED STATES PATENT AND TRADEMARK OFFICE
CERTIFICATE OF CORRECTION

PATENT : 5,625,109

DATED : April 29, 1997

INVENTOR(S) : Vijai P. Gupta

It is certified that error appears in the above-identified patent and that said Letters Patent is hereby corrected as shown below:

On the title page, before item [21]; insert the following:

--[73] Assignee: ARCO Chemical Technology, L. P., Greenville, Del.--.

Signed and Sealed this

Eighteenth Day of November 1997

*Attest:*

BRUCE LEHMAN

*Attesting Officer*      *Commissioner of Patents and Trademarks*